United States Patent
St. Germain et al.

(10) Patent No.: US 8,273,054 B2
(45) Date of Patent: Sep. 25, 2012

(54) SYSTEM AND METHOD FOR ARTERIAL ACCESS

(75) Inventors: Jon St. Germain, Elk River, MN (US); Scott A. Olson, Princeton, MN (US); Daniel J. Klima, Andover, MN (US); John A. Roop, Millbrae, CA (US); Paul J. Thompson, Minnetonka, MN (US)

(73) Assignee: St. Jude Medical Puerto Rico, LLC, Caguas, PR (US)

( * ) Notice: Subject to any disclaimer, the term of this patent is extended or adjusted under 35 U.S.C. 154(b) by 239 days.

(21) Appl. No.: 11/848,461

(22) Filed: Aug. 31, 2007

(65) Prior Publication Data

US 2008/0154190 A1    Jun. 26, 2008

Related U.S. Application Data

(60) Provisional application No. 60/824,376, filed on Sep. 1, 2006.

(51) Int. Cl.
*A61M 25/09* (2006.01)

(52) U.S. Cl. .............. 604/95.04; 604/164.13; 604/525

(58) Field of Classification Search ............ 604/95.04, 604/164.13, 525
See application file for complete search history.

(56) References Cited

U.S. PATENT DOCUMENTS

| | | | |
|---|---|---|---|
| 5,389,090 A | | 2/1995 | Fischell et al. |
| 5,755,687 A | | 5/1998 | Donlon |
| 5,891,057 A | | 4/1999 | Chaisson et al. |
| 6,110,163 A | * | 8/2000 | Voda ........................ 604/523 |
| 6,210,362 B1 | * | 4/2001 | Ponzi ...................... 604/95.01 |
| 7,001,358 B2 | * | 2/2006 | Fitzmaurice et al. ...... 604/96.01 |
| 7,377,906 B2 | * | 5/2008 | Selkee ..................... 604/95.04 |
| 7,402,151 B2 | * | 7/2008 | Rosenman et al. ........ 604/95.05 |
| 7,706,894 B2 | * | 4/2010 | Stewart et al. ............... 607/122 |
| 2002/0004631 A1 | * | 1/2002 | Jenkins et al. ............... 600/374 |
| 2003/0055398 A1 | * | 3/2003 | Imran ........................ 604/510 |
| 2003/0097095 A1 | * | 5/2003 | Brady et al. ............. 604/164.13 |
| 2003/0208141 A1 | * | 11/2003 | Worley et al. ................ 600/585 |
| 2004/0015151 A1 | | 1/2004 | Chambers |
| 2005/0027243 A1 | * | 2/2005 | Gibson et al. ............. 604/95.04 |
| 2005/0080429 A1 | | 4/2005 | Freyman et al. |
| 2005/0234437 A1 | * | 10/2005 | Baxter et al. .................... 606/15 |
| 2006/0135961 A1 | * | 6/2006 | Rosenman et al. ........... 606/108 |
| 2006/0200191 A1 | * | 9/2006 | Zadno-Azizi ................ 606/200 |
| 2007/0179496 A1 | * | 8/2007 | Swoyer et al. .................. 606/41 |
| 2008/0139999 A1 | * | 6/2008 | Gibson et al. ............. 604/95.04 |

FOREIGN PATENT DOCUMENTS

WO        0007656 A1    2/2000

\* cited by examiner

*Primary Examiner* — Theodore Stigell
*Assistant Examiner* — Gerald Landry, II
(74) *Attorney, Agent, or Firm* — Holland & Hart

(57) ABSTRACT

A system for arterial access for delivery of treatment devices is provided. In one embodiment, the system comprises a guidewire and a catheter. The catheter comprises a handle and a shaft. The shaft may be a steerable/deflectable tip shaft with a lumen adapted to allow passage of the guidewire at least partially there through. A passive sheath may also be provided to be delivered over the shaft. The handle controls the steerable/deflectable tip shaft and may be used to deflect the distal tip of the shaft.

17 Claims, 10 Drawing Sheets

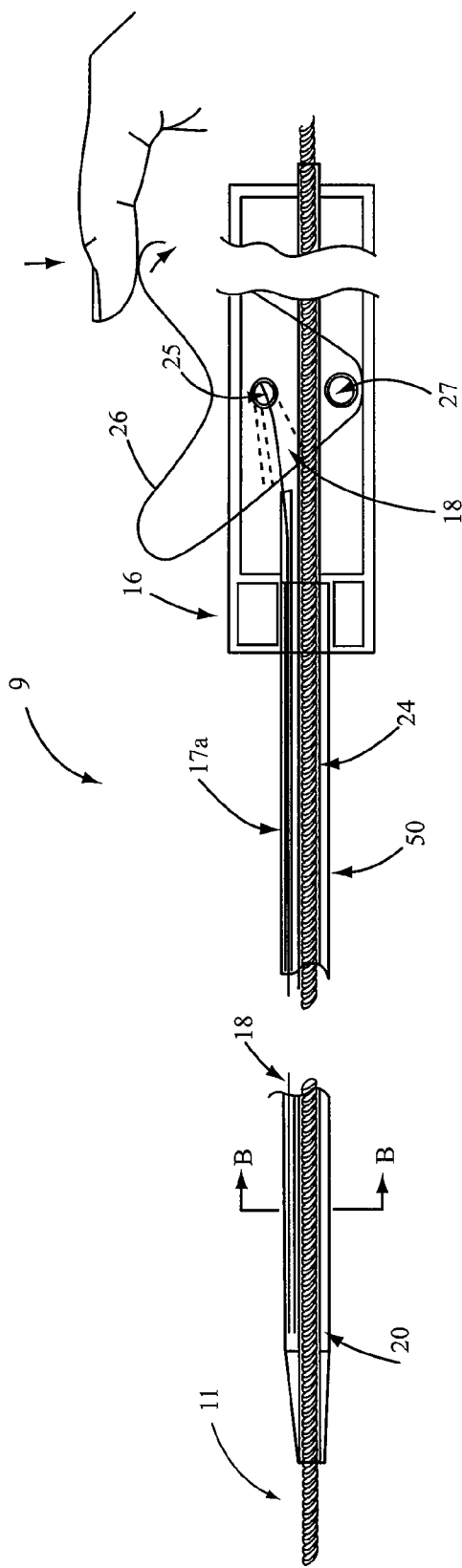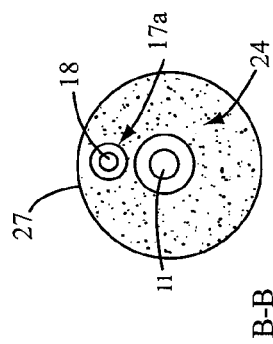
FIG. 4A
FIG. 4B

Section A-A

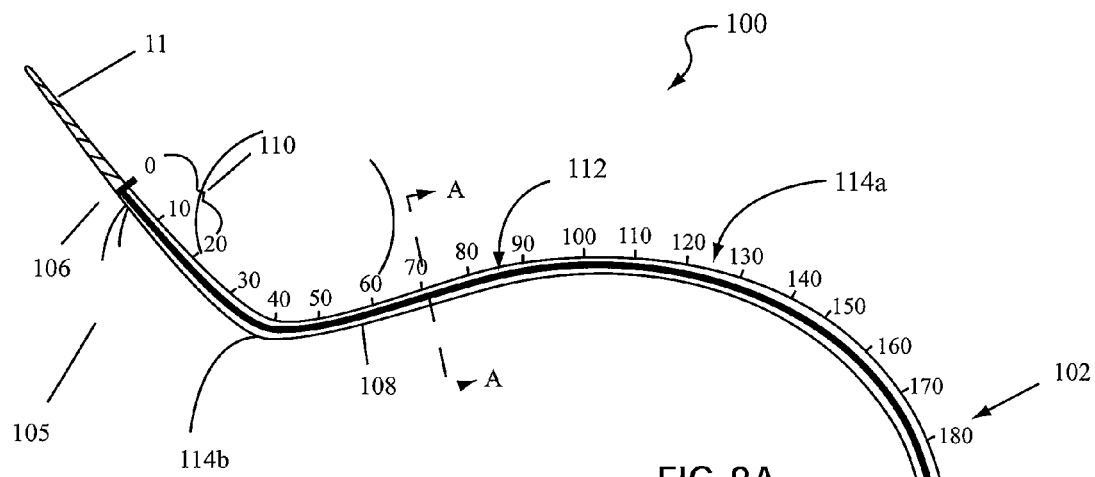
FIG. 8A
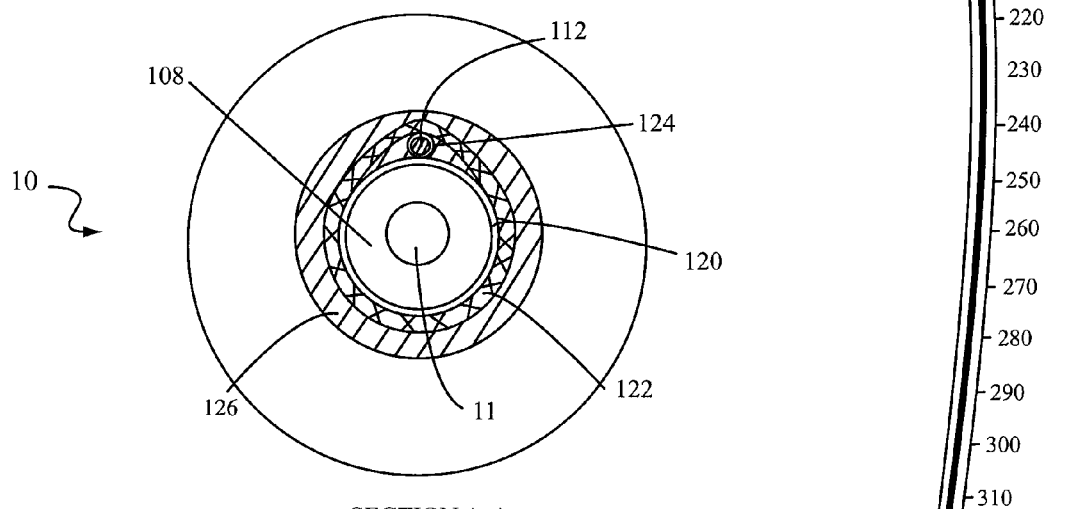
SECTION A-A
FIG. 8B
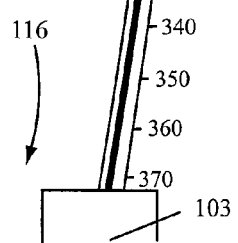

SYSTEM AND METHOD FOR ARTERIAL ACCESS

CROSS REFERENCE TO RELATED APPLICATION(S)

This application claims the benefit of U.S. Provisional Patent Application No. 60/824,376, filed Sep. 1, 2006, the contents of which is incorporated in it's entirety herein by reference.

FIELD OF INVENTION

The present invention relates to systems and methods for obtaining arterial access. More specifically, the present invention relates to systems and methods for obtaining access to a carotid artery from a puncture site in the femoral artery, for example for delivery of treatment devices to treat vascular obstructions in the carotid artery or locations downstream.

BACKGROUND

Arterial disease in humans involves the build up of plaque deposits in arterial walls. The plaque deposits can obstruct blood flow and thus limit the ability of the body to adequately deliver oxygen to tissue. In some instances, blood flow may stop completely. In addition, as flow is diminished, blood clots can form and be released. Plaque rupture may cause loose plaque or a blood clot to migrate down stream to the brain and cause a stroke. Accordingly, it is desirable to treat such plaque deposits (also called lesions) before they cause such problems.

Diagnostic means such as angiography or external ultrasound may be used to determine the extent of arterial disease and may be used to make a recommendation on treatment. Typical treatment may involve a surgical procedure know as carotid endarterectomy whereby plaque is surgically removed, or a less invasive means of treatment called carotid artery stenting. In carotid artery stenting, a nitinol self-expanding cylindrical structure is delivered to the lesion site via an intravascular catheter where the stent is held by the catheter in a collapsed state. A sheath may be used to cover the stent such that, when the sheath is pulled proximally, the stent expands, for example, to press against the inside of the artery. A balloon angioplasty catheter may be used to expand the stent to compress the plaque and restore flow by enlarging the diameter of the artery increasing blood flow at the lesion site. The stent then maintains the enlarged diameter. A nitinol stent (unlike stainless steel stents) has an added benefit that, should the stent be subjected to a collapsing external force, it will restore itself to the previous diameter once the force is removed.

Arterial access for interventional devices such as stent delivery and angioplasty catheters may be achieved through the femoral artery in the groin area. Specifically, access to the carotid arteries may be gained through the femoral artery. The left carotid artery generally extends from the aortic arch to the left side of the neck and into the head. The right carotid artery generally originates as a branch artery from the brachiocephalic trunk which originates at the top of the aortic arch, and extends to the right side of the neck and into the head. Therefore, to reach the carotid artery lesions, catheters must pass from the femoral artery through the descending aorta, into the aortic arch and either directly into the left carotid or through the brachiocephalic artery to the right carotid artery (see FIG. 1).

The treatment of carotid artery disease by stenting is an extension of the prior treatment of coronary artery lesions by stenting. The devices used for access of carotid arteries have their root in those used for coronary angioplasty and stenting. However, the devises used in coronary angioplasty and stenting are not optimal for the more tortuous anatomy of the carotid arteries. Accordingly, efforts have been made to develop devices capable of navigating the anatomy of the carotid arteries.

In coronary angioplasty and stenting, femoral access is typically achieved by use of a needle through the skin to the femoral artery. Blood flowing through the needle indicates that access to the artery has been achieved. This may be referred to as a blood flow indication. One arterial access method, the Seldinger Technique, as applied to accessing the coronary arteries, is as follows:

A guidewire is placed through the needle into the artery and the needle is removed. A dilator and introducer sheath are advanced over the guidewire until the sheath is within the artery. Commonly, the sheath is a 6 French (2 mm inside diameter) sheath, but may be a 5 to 8 French. The dilator and guidewire are then removed. A hemostasis valve, provided at the proximal end of the sheath, may be used to prevent blood loss from the artery.

A guidewire is manipulated through the sheath, through the femoral artery, iliac artery, descending aorta, and aortic arc. A guide catheter with a soft distal tip comprising pre-shaped curve is advanced over the guidewire through the sheath. The guidewire prevents the distal tip from assuming the pre-shaped curve. After advancement of the guide catheter, the guidewire is removed, thus permitting the guide catheter distal end to curve as pre-shaped. The guide catheter is advanced and manipulated until the soft distal tip engages the ostium of the coronary left or right artery. A guidewire is then advanced through the guide catheter and across the lesion. An angioplasty balloon or stent delivery catheter (or other treatment device) is advanced over the guidewire and the stent released in the lesion. Pre or post dilation of the lesion with a balloon catheter may be done over the same guidewire.

A similar technique may be used in accessing the carotid arteries but the curve geometry of the guide catheter and the tortuous pathway through the carotids limits the acceptability/suitability of this approach.

As a result of lower success using a coronary access system, a typical procedure for accessing the carotids now involves the needle access to the femoral artery but places a longer guidewire in the artery before needle removal. The guidewire is advanced to the aortic arch. A diagnostic catheter with a pre-shaped bend in the distal end is advanced over the guidewire until the distal end is near the aortic arch carotid access. The guidewire at this point extends a short distance out the diagnostic catheter distal tip or may be retracted proximally of the curved end of the diagnostic catheter. The diagnostic catheter is manipulated until the distal tip engages the desired artery ostium. The guidewire is then advanced through the carotid artery and the diagnostic catheter is removed. A long dilator having a sheath thereover, is passed over the guidewire into the femoral artery and then advanced into the carotid artery.

An alternative to this procedure is to introduce a long guidewire into the femoral artery, remove the needle, and advance a dilator with a pre-mounted long sheath over the guidewire. The guidewire, dilator, and sheath are then advanced together to a position near the aortic arch. The dilator is removed over the guidewire and a diagnostic catheter is advanced through the sheath over the guidewire until the end of the diagnostic catheter is near the guidewire end (1-2 cm). The diagnostic catheter is advanced and manipulated to gain tip access to the desired ostium and the guidewire is advanced through the diagnostic catheter into the desired carotid artery. The sheath is thus over the diagnostic catheter and guidewire through the carotid artery to a position proximal the lesion of treatment. The guidewire and diagnostic catheter are then removed to allow for introduction of one or more treatment devices.

Although these procedures work for many patients, they are time consuming and involve significant device manipulation and exchanges. Further, these methods of arterial access do not work for all patients. This is typically because of angles at the ostium, anatomical variation, degree of arterial plaque buildup, and/or degree of tortuousity (see FIG. 1). In difficult cases, drag in advancement of the sheath over the diagnostic catheter may cause the diagnostic catheter to prolapse into the aorta, pulling the wire out of the carotid. Similarly a guide catheter may prolapse while attempting to pass a treatment device. This requires a re-start of the procedure for obtaining access. Guide catheters may generally be difficult for use in gaining carotid access due to the size of the aorta, difficulty of engagement into the ostium, and inadequate back up support. Also, because of their size and stiffness, there is a chance that the guide catheter or diagnostic catheter may dislodge plaque in the ostium and cause a stroke from the embolism before a filter can be deployed up stream to capture emboli.

Accordingly, there is a need for an improved systematic approach to carotid artery access.

SUMMARY OF THE INVENTION

Systems and methods for obtaining arterial access to and from a puncture site are provided. More specifically, systems and method are provided for obtaining carotid artery access through the femoral artery for delivery of treatment devices to treat vascular obstructions in the carotid arteries or downstream.

In one embodiment, a system for arterial access for delivery of one or more treatment devices is provided. The system comprises a guidewire, a handle, a shaft, and a sheath. The shaft has a proximal end and a distal end, the proximal end being coupled to the handle and a distal segment of the shaft proximate the distal end being deflectable. The shaft has a preset curvature and has a lumen for receiving the guidewire at least partially therethrough. The sheath is adapted to be delivered over the shaft.

A further embodiment of a system for arterial access for delivery of one or more treatment devices is provided comprising a guidewire, a handle, a shaft, first and second pullwires, and a sheath. The shaft has a proximal end and a distal end, the proximal end being coupled to the handle and a distal segment of the shaft proximate the distal end being deflectable. The shaft has a lumen for receiving the guidewire at least partially therethrough. The first and second pullwires are associated with the shaft, the first pullwire being coupled to the shaft proximate the distal end of the shaft and the second pullwire being coupled to the shaft proximally of the distal end of the shaft, the first and second pullwires effecting a curvature of the shaft. The sheath is adapted to be delivered over the shaft.

In a further embodiment, a method of treating carotid artery lesions is provided. A system comprising a guidewire, a shaft having a preset curvature, a deflectable tip, and a lumen for passage over the guidewire, and a sheath sized for placement over the shaft is provided. A femoral artery is access with a needle. The guidewire is placed through the needle and into the femoral artery. The needle is removed. The shaft, having the sheath overlying the shaft, is advanced over the guidewire and into and through the femoral artery to an aortic arch. The shaft is manipulated to direct the deflectable tip toward the ostium leading to a right or a left carotid artery. The guidewire is advanced through the ostium into the carotid artery. The shaft is advanced over the guidewire into the carotid artery. The sheath is advanced over the shaft and into the carotid artery. The guidewire and shaft are removed. One or more treatment devices are introduced through the sheath the one or more carotid lesions are treated, the treatment devices are removed from the sheath; the sheath is removed, and the puncture site is sealed at the femoral artery.

In yet a further embodiment, a method of establishing femoral access to the carotid artery, suitable for passage of carotid artery lesion treatment devices is provided. A system comprising a guidewire, a shaft having a lumen for passage over the guidewire, wherein the shaft may be manipulated to preset curvature, and a sheath sized for placement over the shaft is provided. The femoral artery is accessed with a needle. A guidewire is placed through the needle and into the femoral artery. The needle is removed. The shaft, with the sheath overlying the shaft, is advanced over the guidewire and into and through the femoral artery to an aortic arch. The shaft is manipulated to direct the deflectable tip toward the ostium leading to a right or a left carotid artery. The guidewire is advanced through an ostium into a carotid artery. The sheath is advanced over the shaft and into the carotid artery and the guidewire and shaft are removed.

In another embodiment, an arterial access system is provided. The arterial access system comprises a handle and a shaft. The shaft comprises a distal end and a proximal end, wherein the shaft has varying stiffness along a length thereof, being most stiff at the proximal end and least stiff at the distal end, a pre-set passive shape along the length of the shaft, and a distal tip at the distal end of the catheter, wherein the distal tip may be deflected by actuation of the handle.

BRIEF DESCRIPTION OF THE DRAWINGS

The foregoing and other objects, features and advantages of the invention will be evident to those skilled in the art from the detailed description of the invention, below, taken together with the accompanying drawings, in which:

FIG. 4a is a partial cutaway drawing taken along the longitudinal axis of an arterial access system comprising a handle and a shaft in accordance with a further embodiment.

FIG. 4b is a cross-sectional view of a shaft of the arterial access system of FIG. 4a in accordance with one embodiment.

FIG. 8a is a perspective view of an arterial access system including a shaft having a preset shape in accordance with one embodiment.

FIG. 8b is a cross-sectional view of the shaft of FIG. 8a in accordance with one embodiment.

DETAILED DESCRIPTION OF THE INVENTION

The following description is not to be taken in a limited sense but is merely for the purpose of describing the general principles of the invention whose scope is defined by the appended claims.

Throughout this description the word proximal refers to a position external of the body or the operator and the word distal refers to a position internal to the body and away from the operator.

Figure 1:
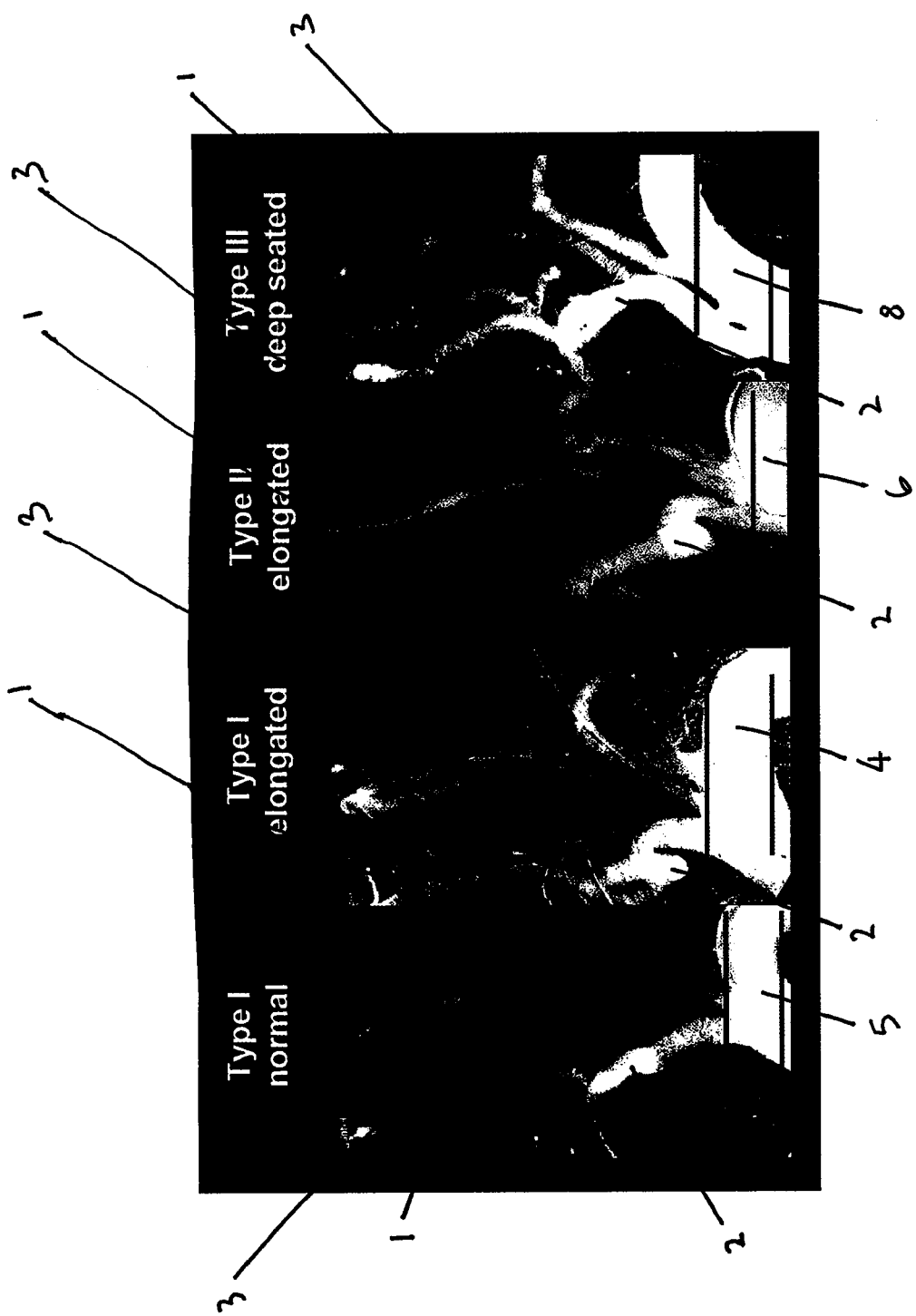
FIG. 1 shows angiographic images for four variations of human anatomy of the aortic arch along with the brachio, brachiocephalic and carotid arteries.

Referring to FIG. 1, the diversity of vascular anatomy of the human arterial system directly above the heart can be appreciated. The right carotid artery 1 is normally a branch-off from the brachiocephalic artery 2 which rises from the aortic arch (type 1 normal 2). The left carotid artery 3 is a direct take off from the aortic arch. The area of treatment for carotid disease is near the branch of the carotid arteries 1, 3 where the carotid artery separates into the internal and external carotid arteries in the neck region (top of photos). FIG. 1 represents a normal aortic arch 5 (Type I normal) and a variety of aortic arch anomalies including Type I elongated 4, Type II elongated 6, and Type III deep seated 8. See *Carotid Artery Interventions: Fundamental Principles and Techniques*, Daniel J. McCormick. These anomalous aortic arches 4, 6, 8 can complicate gaining access to the carotid arteries 1, 3. For example, in some cases the left carotid 3 artery may branch from the brachiocephalic artery 2 instead of the aorta (Type III deep seated). In other cases the brachiocephalic take off may be closer to the aortic valve making access a sharp angle take off from the aorta when access from the femoral artery is chosen. Attempting to use conventional pre-set curved guide catheters can be difficult because advancement of a treatment device through the guide curve may cause the guide to be pushed toward the aortic valve and prolapse out of the desired ostium.

Figure 2A:
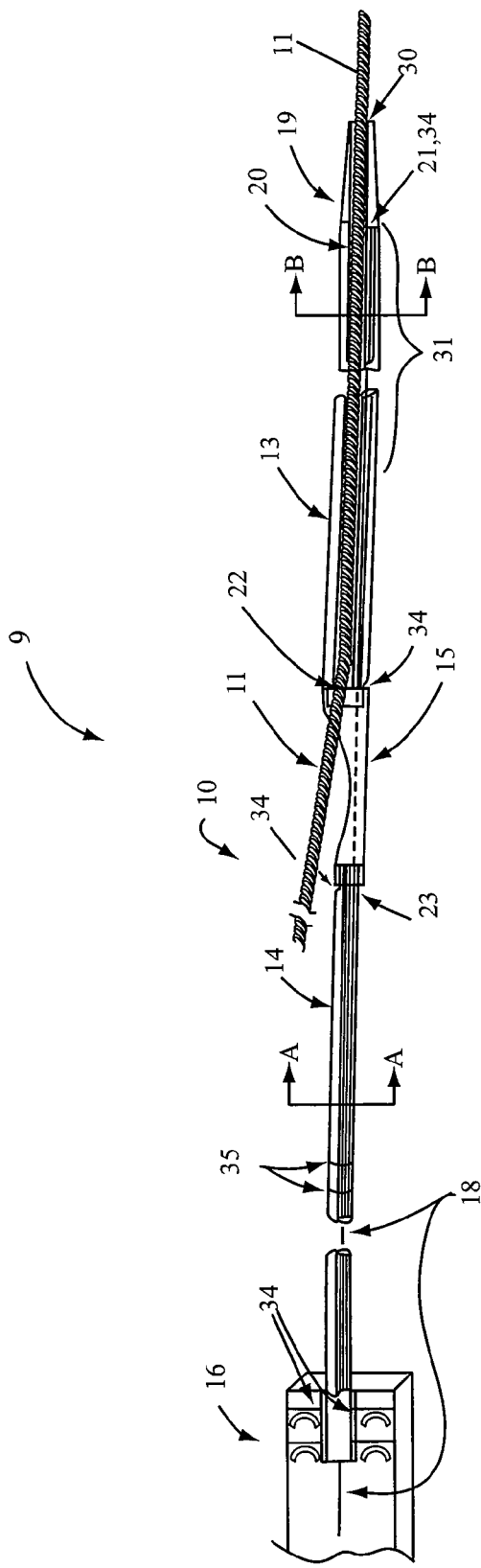
FIG. 2a is a partial longitudinal cutaway of an arterial access system comprising a handle and a shaft in accordance with one embodiment.
Figure 2C:
FIG. 2c is a cross-sectional view of a distal shaft portion of the shaft of FIG. 2a in accordance with one embodiment.
Figure 2B:
FIG. 2b is a cross-sectional view of a proximal shaft portion of the shaft of FIG. 2a in accordance with one embodiment.

FIGS. 2a-2c show an arterial access system including a steerable/deflectable tip catheter in accordance with one embodiment. The catheter system 9 comprises a handle 16 and a shaft 10. The shaft 10 comprises a proximal shaft portion 14 extending distally from the handle 16, and a distal shaft portion 13 connected to and extending distally from the proximal shaft portion 14. The proximal end of the proximal shaft portion 14 is coupled to the distal end of the handle 16. The catheter system 9 uses a pullwire 18 attached to an actuator in the handle 16 at the proximal end of the pullwire 18 to effect curvature of a distal segment 31 of the distal shaft portion 13. The distal segment 31 may be preshaped such that pulling the pullwire 18 effects a predictable curvature of the distal segment 31. The pullwire 18 extends through a lumen 17 (see FIG. 2b) in the proximal shaft portion 14, through a lumen 17a (see FIG. 2c) in the distal shaft portion 13 to a location 21 proximal to the distal end 30 of the distal shaft portion 13. Actuation of the actuator in the handle 16 pulls or pushes the pullwire 18 and deflects, or curves, the distal segment 31 of the shaft 10. The shaft 10 has two lumens, one lumen 24 for a guidewire 11 and one lumen 17, 17a for the pullwire 18. In the embodiment of FIGS. 2a-2c, the guidewire lumen 24 extends through the distal shaft portion 13. In alternative embodiments, such as shown in FIGS. 4a and 4b, the guidewire lumen 24 may extend through the length of the shaft. The catheter system 9 may be used with a passive sheath 12 (see FIG. 6). More specifically, a passive sheath 12 may be provided over the shaft 10. The sheath 12 may be used to control curvature of the distal segment 21 of the shaft 10. In various embodiments, the shaft 10 serves as a dilator for access through the skin into the femoral artery after needle puncture and guidewire placement in the artery. Accordingly, when access is initially gained using the Seldinger Technique, no separate dilator is required. FIGS. 4a and 4b illustrate an alternative embodiment of the steerable/deflectable tip catheter having a single shaft portion 50 in lieu of a proximal shaft portion 13 and a distal shaft portion 12. In general, description of use of the catheter is the same for the embodiment shown in FIGS. 2a-2c and the embodiment shown in FIGS. 4a and 4b.

The arterial access system described herein may be used to provide access to the carotid arteries. In some embodiments, such access involves a needle puncture through the skin to the femoral artery, followed by placement of a guidewire 11 (for example, a 0.035/0.038 in. guidewire), and removal of the needle. The passive sheath 12 (FIG. 6) is loaded over the shaft portion or portion 10 (13, 14) or 50 of the catheter 9 such that the distal end 30 of the shaft 10 extends distally of the distal tip of the sheath 12. The shaft 10 may be provided with a dilator tapered tip 19 at the distal end of the distal shaft portion 13 that bridges the diameter from the guidewire lumen 24 to the sheath 12 diameter and has sufficient stiffness and taper angle to be advanced over the guidewire 11, through the subcutaneous tissue, and through the needle puncture in the artery, stretching the artery opening to allow entry of the shaft 10 and sheath 12 into the artery.

The guidewire 11 may be advanced up the femoral artery, iliac artery, and descending aorta to the aortic arch. Holding the guidewire 11 stationary, the combined shaft 10 and sheath 12 may be advanced over the guidewire 11 until positioned near the ostium of the desired aortic takeoff to access the carotid artery. At this point the guidewire 11 is positioned such that the distal tip of the guidewire is several centimeters inside the distal segment 31 of the shaft 10. The handle 16 is manipulated to pull on the pullwire 18 to deflect or curve the distal segment 31 of the catheter 9. The distal segment 31 of the shaft 10 may be visualized to assess orientation. If the deflected distal segment 31 is not oriented correctly, the handle 16 may be manipulated to position the distal segment 31 in the desire direction toward the desired ostium. The degree of bend of the distal segment 31 of the shaft 10 may, in some embodiments, be controlled by the degree of pull on the pullwire 18 by handle manipulation.

Once the angle and position of the distal segment 31 of the shaft 10 is as desired, the shaft 10, sheath 12, and guidewire 11 may be advanced into the desired arterial ostium. The guidewire 11 may be advanced through the carotid near the lesion for additional support. Once the ostium is at least partially accessed, the bend in the distal segment 31 of the shaft 10 may be relaxed by handle manipulation to avoid damage to the wall of the artery. The shaft 10 and sheath 12 may be advanced to the point of the next bend and the shaft 10 again used in the same manner to cross this bend. The sheath 12 may be advanced independently of the shaft 10 and advanced as far as desired over the guidewire 11 to a point proximal the lesion of interest/treatment.

Once the sheath 12 is positioned proximate the lesion of interest/treatment, the catheter 9 and guidewire 11 may be removed to allow the sheath 12 to be used for delivery of a treatment device such as a percutaneous transluminal coronary angioplasty (PTCA) balloon or stent delivery system. These devices are usually delivered over a 0.014 in. guidewire. Once treatment is complete, the treatment device (s), guidewire (if used), and sheath 12 are removed and the femoral access puncture site sealed.

Discussion is now made of the components of the arterial access system including a steerable catheter comprising a handle 16 and shaft 10.

As shown in FIG. 2a, the distal end of the pullwire 18 is coupled to the distal shaft portion 13 near the distal tip at 21. Axial movement of the pullwire 18 toward the handle 16 causes the distal segment 31 of the distal shaft portion 13 near the to curve proportionally to the degree of pullwire 18 movement.

In the embodiment shown in FIG. 2a, the proximal shaft portion 14 of the shaft 10 can be made from a multi-layer polymer extrusion. Accordingly, a polymer such as Hytrel® (polyether-ester block copolymer from DuPont,) may be extruded in a manner including a pullwire lumen 17 sized for free axial movement of the pullwire 18. Referring to FIG. 2b, a stainless steel wire 27 section A-A (for example, ranging from 0.001 to 0.003 in. in diameter) may be braided over the extrusion and a second layer of Hytrel® may be extruded over the braided wire to create a composite structure. In one embodiment, the overall wall thickness of the composite structure may be from 0.006-0.020 in. The composite structure has shaft stiffness such that it is pushable through vasculature, shaft flexibility such that it may be passed through bends in the vasculature, and shaft torque-ability such that it may translate twisting motion of the handle to the distal end 30 of the distal shaft portion 13. This technology is well known in the art of making guide catheters. Other polymers may be used in addition to or in lieu of Hytrel®, such as nylon, polyimide, polypropylene, polyurethane, high density polyethylene, polyether block amide, polybutylene terephthalate, polymer blends, or any other polymer suitable for use in a lumen. U.S. Pat. No. 5,221,270, entitled "Soft Tip Guiding Catheter by Parker," and U.S. Pat. No. 5,658,263, entitled "Multisegmented Guiding Catheter for Use in Medical Catheter Systems" by Dang et al., describe such construction techniques and are herein incorporated by reference in their entireties. Various grades of Hytrel® are available for varying the stiffness/flexibility of the proximal shaft portion 14. It is to be appreciated that all materials and specifications are intended for illustrative purposes only and are not limiting.

As an alternative, or in addition, to the Hytrel® inner layer, a thin PTFE (polytetrafluoroethylene) layer may be provided to form an inner surface of the proximal shaft portion 14 of the shaft 10 Another embodiment may comprise a non-extrusion wall construction of a matrix of PTFE on the inner surface of the proximal shaft portion 14. Description of this embodiment starts at the center of the shaft and moves outwardly. The inner layer comprises PTFE. The PTFE inner surface may be covered by polyimide and braided wire. Multiple thin layers of polyimide may be provided as the outer surface.

In some embodiments, the pullwire 18 may comprise a stainless steel wire or plurality of wires having a diameter from, for example, approximately 0.003 to approximately 0.010 in diameter and from one to 20 wires in a strand or braid. In one embodiment, the pullwire 18 comprises a stainless steel wire having a 0.005 in. diameter. The pullwire 18 may alternatively comprise a generally flat ribbon having, for example, approximately a 0.003 in. by 0.010 in. cross-section. The proximal shaft portion pullwire lumen 17 (see FIG. 2b) may generally be approximately 0.002-0.004 in. larger in dimension than the pullwire 18 in order to provide low friction for axial movement of the pullwire 18 through the lumen 17. Further, the pullwire 18 may be PTFE coated to reduce friction in the lumen 17. Alternatively, the pullwire lumen 17 may have an inside coating of PTFE and the pullwire uncoated. In yet another embodiment, both the pullwire 18 and the pullwire lumen 17 may have a PTFE coating (or other coating to reduce friction).

The proximal shaft portion 14 may have an outer diameter ranging from, for example, 0.26 to 0.047 in. While any suitable dimensions may be used, in one embodiment, the outer diameter may be between 0.0038 and 0.041. The proximal shaft portion 14 may be sized for use with, for example, a 6 French I.D. passive sheath (see sheath 12 of FIG. 6). As is known in the art, a 6 French I.D. passive sheath generally has an inner diameter of 0.079 to 0.087 in. The proximal shaft portion 14 is generally smaller than the distal shaft portion 13 to allow room for the guidewire 11 to pass along side the proximal shaft portion 14 while in the 6 French passive sheath 12. This allows for clearance between the inside diameter of the passive sheath 12 and the outside diameters of the proximal shaft portion 14 and the distal shaft portion 13 of the shaft 10 for ease of passage of the sheath over the proximal shaft portion 14 and the distal shaft portion 13 of the shaft 10. A stainless steel wire 27 (see FIGS. 2a and 3) may be used for braiding the proximal shaft portion 14 and may be, for example, 0.001-0.003 in. in diameter, but may vary, for example, between 0.0005 in. and 0.0004 in. in diameter. The length of the proximal shaft portion 14 may vary, for example, from 50 to 90 cm. In one embodiment, the proximal shaft portion 14 is approximately 70 cm in length. The length of the distal shaft portion 13 may vary, for example, between 10 and 40 cm. In one embodiment, the distal shaft portion 13 is approximately 30 cm in length. In some embodiments, the combined length of the proximal shaft portion 14 and the distal shaft portion 13 may be range from, for example 90 cm to 150 cm. In one embodiment, the combined length of the proximal shaft portion 14 and the distal shaft portion 13, and thus the overall length of the shaft 10, is 100 cm. This may be referred to as the working length of the catheter.

As shown in FIGS. 2a and 2c, the distal shaft portion 13 of the steerable/deflectable tip catheter 9 has a central guidewire lumen 24. The distal shaft portion 13 may be sized to fit a 0.035-0.038 in. guidewire 11 and a pullwire lumen 17a. The distal shaft portion 13 has a distal segment 31 that provides steering function and may be from approximately 1 to approximately 20 cm in length, from approximately 2 to approximately 10 cm in length, or other suitable length. The pullwire lumen 17a and/or the guidewire lumen 24 may be eccentric. Generally, the pullwire lumen 17a may be sized to permit the pullwire 18 to move freely in the axial direction. The distal shaft portion 13 may comprise a Hytrel® dual lumen extrusion of 0.008-0.016 in. wall thickness with a stainless steel 0.001-0.003 in. diameter wire braid 27a around the lumen 17a and lumen 24. A Hytrel® extrusion may be layered over the wire braid 27a.

The distal portion of the pullwire 18, the portion residing in the pullwire lumen 17a of the distal shaft portion 13, may optionally be flattened or ground. In one embodiment, the pullwire 18 is flattened to 0.002 in. by 0.005 in. In another embodiment, the pullwire is ground to 0.002-0.003 in. diameter. Such flattening or grinding reduces the size of the pullwire lumen 17a and thus permits provision of an optional restoring force element (described later with reference to FIG. 5) while maintaining the overall distal shaft diameter at approximately 0.076-0.084 in. for a 6 French carotid access system. The dimensions may of course vary based on the system French size, such as for 5-8 French systems. Generally, the guidewire lumen 24 may be sized to be approximately 0.002-0.004 in. larger than the largest guidewire diameter, or about 0.040-0.042 in. In some embodiments, the guidewire lumen 24 may be a short lumen provided proximate the distal end 60 of the distal shaft portion 13 of the shaft 10 to enhance ease of removal over the guidewire 11. The short wire lumen reduces wire drag for advancement of the proximal shaft portion 14 and distal shaft portion 13 over the guidewire 11. In alternative embodiments, such as shown in FIG. 4b, a full length guidewire lumen may be provided. Various grades of Hytrel® are available for varying the stiffness/flexibility of the distal shaft portion 13. As previously noted, in some embodiments, the proximal shaft portion 14 may generally be smaller in diameter than the distal shaft portion 13. This difference in diameter size allows room for the guidewire 11 to pass along side the proximal shaft portion 14 while in the 6 French passive sheath 12. This allows for clearance between the inside diameter of the passive sheath 12 (FIG. 6) and the outside diameters of the proximal shaft portion 14 and the distal shaft portion 13 of the shaft 10 for ease of passage of the sheath over the proximal shaft portion 14 and the distal shaft portion 13 of the shaft 10. Also the smaller proximal shaft portion 14 allows greater cross-section open area and less flow resistance for saline, drug, or dye injections between the sheath 12 and proximal shaft portion 14.

As shown in FIG. 2a, a transition member 15 may be provided to couple the proximal shaft portion 14 and the distal shaft portion 13. Coupling may be achieved, for example, by epoxy adhesive. In one embodiment, the transition member 15 comprises a tube with a portion of the circumference removed as by machining, to allow a guidewire (for example, a 0.035-0.038 in. guidewire) to enter the generally central guidewire lumen 24 in the distal shaft portion 13. The transition member 15 may be formed of any suitable material including, for example, nitinol, stainless steel, or a polymer. The diameter of the tube of the transition member 15 may be selected to be approximately the same as the shaft diameter of the proximal shaft portion 14 or the distal shaft portion 13 where the proximal shaft portion 14 or distal shaft portion 13 engage the transition member 15. Accordingly, in some embodiments, the diameter of the transition member 15 tube may vary from its proximal end (engaging the proximal shaft portion 14) to its distal end (engaging the distal shaft portion 13). A short section of braid 27, 27a may be removed from the proximal shaft portion 14 and/or the distal shaft portion 13 where the respective shaft portion engages the transition member 15 such that the distal end of the proximal shaft portion 14 and the proximal end of the distal shaft portion 13 may be placed inside the transition member 15 inside diameter and coupled to the transition member 15. Coupling may be done by applying epoxy at each end 22 and 23 of the transition member 15 or applying epoxy to the proximal end of the distal shaft portion 13 and the distal end of the proximal shaft portion 14. The transition member 15 may be tapered from both ends 22 and 23 to allow the transition member some degree of flexibility and to provide clearance for guidewire access to guidewire lumen 24. The proximal and distal shaft portions 14 and 13 are aligned with the transition member 15 such that the pullwire lumens 17, 17a from each shaft portion are aligned.

Alternative transition member designs may be used. For example, in some embodiments, the proximal shaft portion 14 may be relatively smaller than the distal shaft portion 13 and the transition member 15 may be designed to accommodate such relative sizing. Such transitions are common in the art of rapid exchange catheters. U.S. Pat. Nos. 5,217,482, entitled "Balloon Catheter with Distal Guidewire Lumen by Keith," and 5,061,273, entitled "Angioplasty Apparatus Facilitating Rapid Exchange," by Yock are representative of alternative connection means and are incorporated herein by reference in their entireties.

The pullwire 18 may be bonded to the distal shaft portion 13 near the distal end 30 of the distal shaft portion 13 by epoxy adhesive 34 at location 21. A long polymer tapered distal tip 19 may be bonded to the distal tip of the distal shaft portion 13 to ease passage through the subcutaneous tissue during introduction into the femoral artery and to reduce arterial damage from catheter contact during navigation. Generally, the polymer tapered distal tip 19 may not include a wire braid or other reinforcing structure.

One or more radiopaque marker bands 20 may be added near the distal tip 19 and along distal segment 31 to allow for easy identification of the catheter orientation by angiographic assessment. The distal marker band 20 may additionally or alternatively serve as a base for attachment of the pullwire 18 by adhesive 34, solder, brazing, welding, or other. In an alternative embodiment of a marker, radiopaque filler such as barium sulfate or tungsten may be added to the Hytrel® shaft during extrusion to aid in angiographic viewing of the shaft 10.

Figure 3:
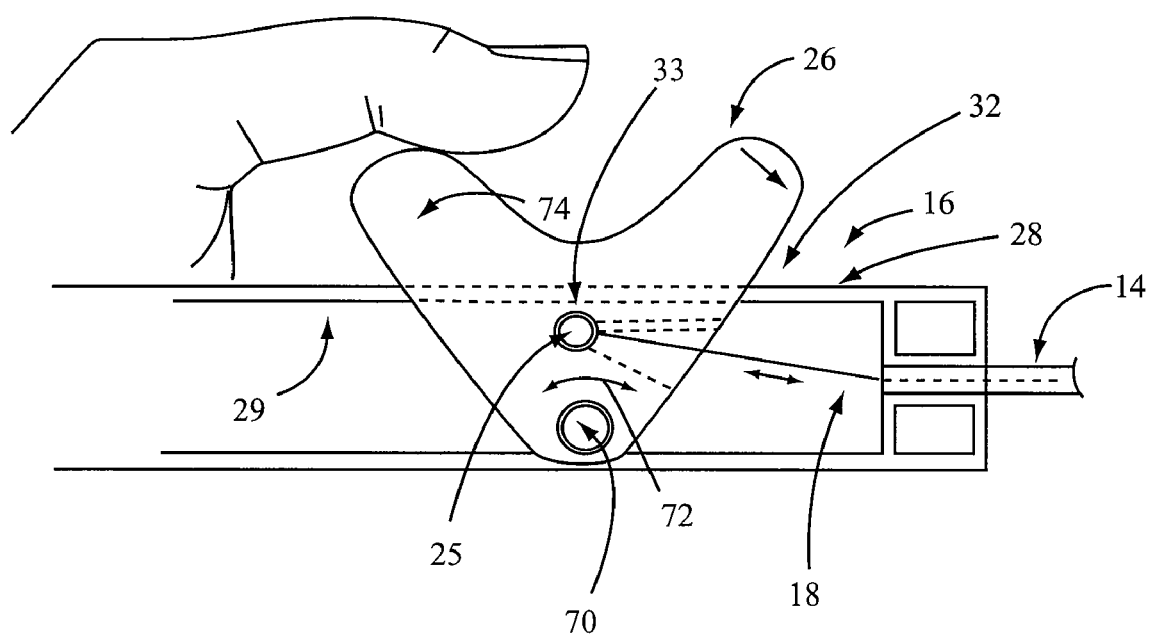
FIG. 3 is a partial cut away drawing taken along the longitudinal axis of the handle of FIG. 2a in accordance with one embodiment.

FIG. 3 illustrates a handle 16 of the arterial access system. In the embodiment shown, the handle 16 includes an actuator 26 that attaches to the proximal end of the pullwire 18 for actuating the pullwire 18 in an axial back-and-forth direction along the pullwire lumen 17 and 17a (FIGS. 2a and 2b respectively). The proximal end of the proximal shaft portion 14 may be bonded to the distal end of the handle 16 with epoxy 34 in a cylindrical cavity formed by two halves of the handle 16.

FIG. 4a illustrates the engagement of the handle 16 with a shaft portion 50 of an alternative embodiment of the catheter 9, discussed more fully below. FIG. 3 shows an actuator 26 and one of two molded halves 32 of the handle 16. The actuator 26 attaches to the pullwire 18 and pivots about a cylindrical post 70 in one half of the handle 16. The actuator 26 has a cylindrical hole 33 which mates with a cylindrical barrel 25 that is swaged or bonded on to the pullwire 18. Rotation of the actuator 26, shown along arrow 72 of FIG. 3, moves the pullwire 18. As can be appreciated from FIG. 3, downward thumb pressure (see arrow 74) applied to the actuator 26 rotates the actuator proximally along arrow 72 and thus pulls the pullwire 18 proximally. Proximal movement of the pullwire 18 causes the distal end of the distal segment 31 of the shaft 10 to form a curved distal shaft shape proportional to the degree of actuation. The distal segment 31 may be generally softer than other portions of the shaft 10 and/or may be preshaped such that curvature is easily achieved in the distal segment 31.

Figure 7A:
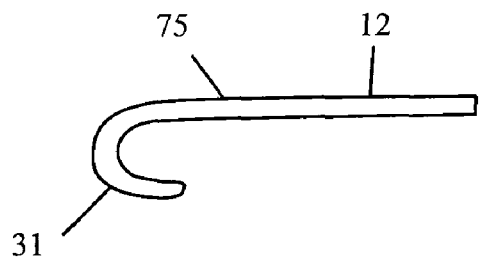
FIG. 7a is a perspective view of a first curve shape of a distal end of an arterial access system in accordance with one embodiment.
Figure 7B:
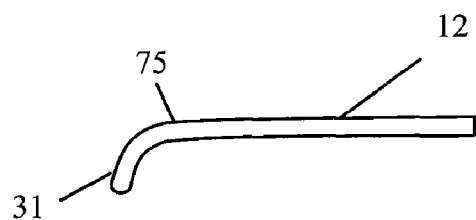
FIG. 7b is a perspective view of a second curve shape of a distal end of an arterial access system in accordance with one embodiment.
Figure 7C:
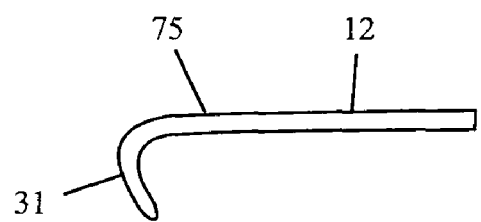
FIG. 7c is a perspective view of a third curve shape of a distal end of an arterial access system in accordance with one embodiment.

Various curve shapes of the distal segment 31 are shown in FIGS. 7a-7c. FIGS. 7a-7c illustrate relative positioning of the passive sheath 12, the distal segment 31, and thus the interface 75 of the passive sheath 12 with the distal segment 31. The curvature of the distal segment 31 are at least partially based on the position of the sheath 12 relative to the shaft 10. Placing the distal end of the sheath 12 nearer the distal end of the shaft causes the distal end of the shaft to form a tighter curve.

Returning to FIG. 3, the degree of actuation by the actuator 26 may be controlled by rotation stops 28 and 29. As a result, the degree of the curve of the distal end of the distal shaft portion 13 may further or alternatively be controlled by placement of rotation stops 28 and 29 at handle 16. In various embodiments, the shaft 10 may have a radiopaque filled wall for the distal 1-5 cm, multiple marker bands of platinum near the distal tip, or other indicators, so that the distal tip shape is clearly visible by angiographic means. The handle may also have radially placed markers to visually indicate the rotational position of the deflectable tip relative to the handle.

Examples of steerable handle mechanisms used to pull one or more wires include U.S. Pat. Nos. 5,275,151; 5,395,329; 5,185,004; 5,195,968, all herein incorporated by reference in their entireties.

Figure 5A:
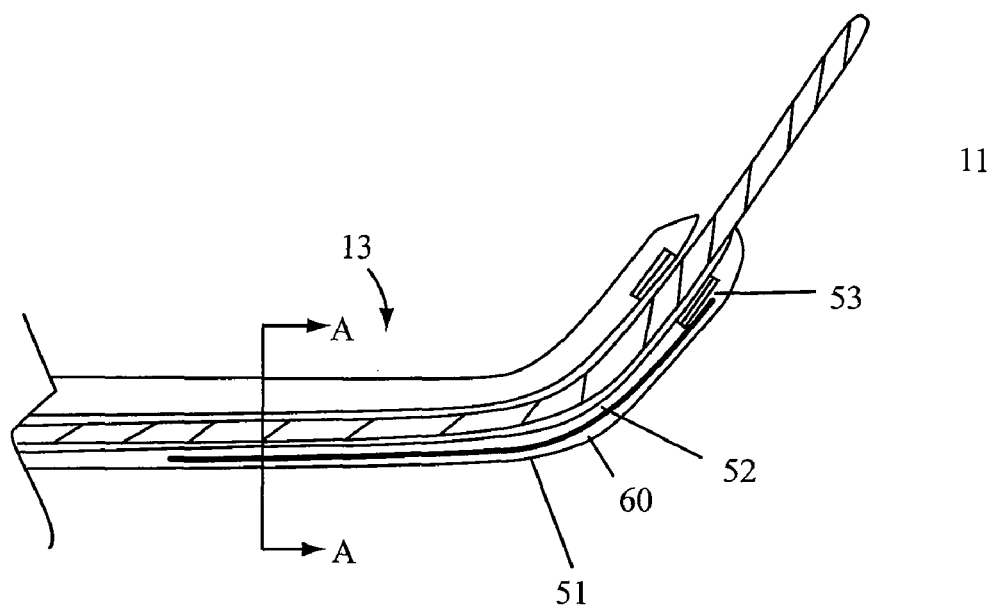
FIG. 5a is a cutaway along the longitudinal axis of the distal end of a shaft including a nitinol ribbon embedded in the wall for providing straightening restoring force, in accordance with one embodiment.
Figure 5B:
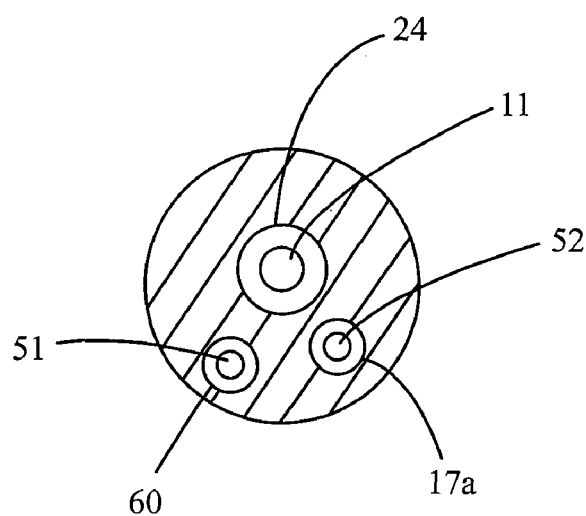
FIG. 5b is a cross-sectional view of the shaft of FIG. 5a in accordance with one embodiment.

FIGS. 5a and 5b illustrate an alternative embodiment of the distal end of the distal shaft portion 13 including a restoring force member. As shown, the guidewire 11 extends through the distal shaft portion 13 and out the distal end of the distal shaft portion 13. The restoring force member may be, for example, a wire or ribbon embedded in the wall of the distal shaft portion 13 to provide straightening restoring force when the pullwire 52 is relaxed following pull activation. The restoring force overcomes any set that may occur in the wall material after extended periods of bend stress in the wall. Referring specifically to the embodiment of FIG. 5a, the distal end includes a stationary restoring force member 51. The stationary restoring force member 51 may be manufactured of nitinol (example 0.003 by 0.010 in. ribbon or 0.005-0.020 in. diameter wire), which is incorporated into the wall on the distal shaft portion 13. Materials other than nitinol may also be used, such as stainless steel or Elgiloy. The restoring force member 51 serves as a straightening mandrel to help restore straightness to the distal end of the distal shaft portion 13 after relaxation of tension on the pullwire 52. Pullwire 52 operates much like pullwire 18 of FIG. 3 and is attached to the distal end of distal shaft portion 13 via pull collar 53. The pull collar 53 may be configured as an embedded ring for attaching to pullwire 52. The restoring force member 51 may be incorporated by extrusion of the distal shaft portion 13 with a third lumen 60 (see FIG. 5b).

FIG. 5b illustrates relative positioning of the three lumens 24, 17a, and 60 in accordance with one embodiment. The guidewire is provided within lumen 24. The pullwire 52 is provided within the lumen 17a. The restoring force member 51 is provided within the lumen 60. In this embodiment, the lumen 60 may be configured to retain the restoring force member 51 in its place, the restoring force member 51 may be bonded to the distal shaft portion 13 under the braid (see 27a of FIG. 2a), or the restoring force member 51 may be incorporated in the wall of the lumen 60 during extrusion of the lumen. In another embodiment the restoring force member 51 may extend proximally across the junction between the proximal shaft portion 14 and the distal shaft portion 13 (see FIG. 2a) to provide flexibility and support in the junction to prevent kinking at the transition member 15. In another embodiment the restoring force member may comprise a distal extension of the transition member 15. In such embodiment, the transition member 15 may extend distally in a ribbon shape and may be bonded to the outside diameter of the distal shaft portion 13.

FIGS. 4a and 4b illustrate a further embodiment of the arterial access system 9. As shown, the proximal and distal shaft portions of the catheter 9 are combined into one shaft 50 with the shaft 50 generally having the construction of the distal shaft portion 13 as previously described with reference to FIGS. 2a-2c. In the embodiment of FIGS. 4a and 4b, there is no transition member 15 and the guidewire lumen 24 passes through the shaft 50 and through the handle assembly 16. Accordingly, in the embodiment of FIG. 4b, the shaft 50 has a full length guidewire lumen 24. Construction is otherwise similar to FIGS. 2a-2c and 3 using similar adhesive and similar handle mechanisms may be used.

Figure 6:
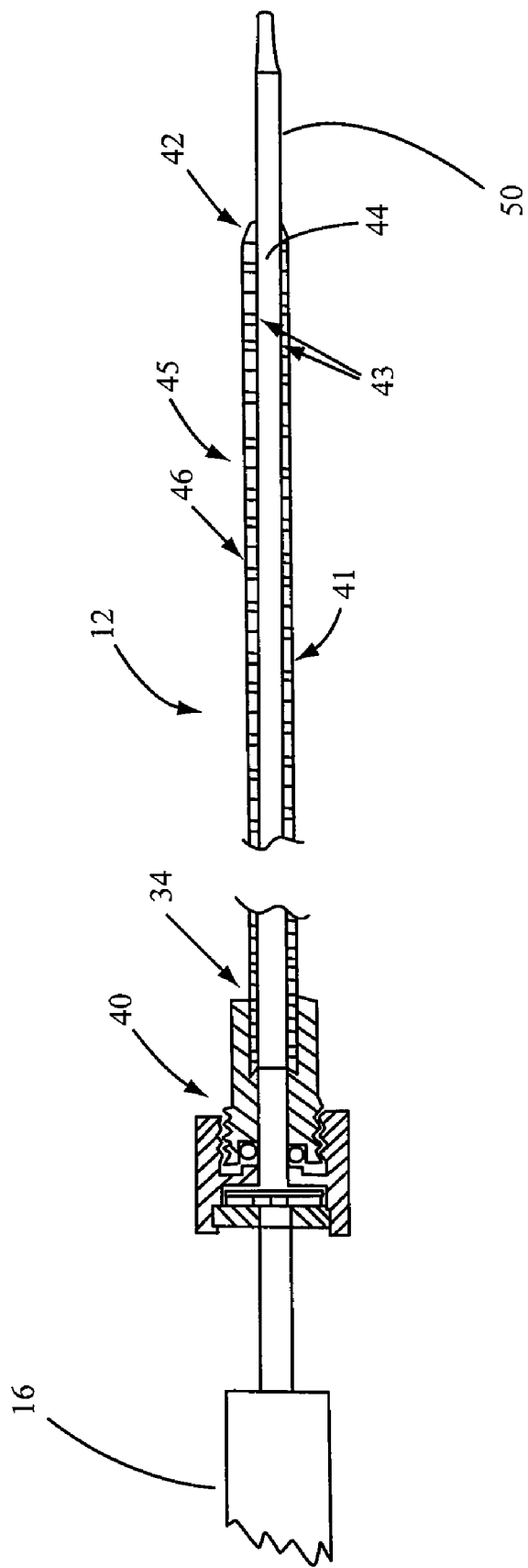
FIG. 6 is a partial cut away drawing of a passive sheath and arterial access system in accordance with one embodiment.

Referring to FIG. 6, the combined length of the sheath 50 (FIG. 4a) or the sheath 10 (FIG. 2a) is generally longer than the length of the passive sheath 12 so that the sheath 12 may be advanced over the shaft 10, 50 through arterial passages. The shaft 10, 50 may include markings 35 to indicate the position of the distal tip of the sheath 12 relative to the distal tip of the shaft 10, 50. For example, in an embodiment comprising shaft 10 having a proximal shaft portion 14 and a distal shaft portion 13, the most distal mark 35 on the proximal shaft portion 14, when lined up with a proximal hub of the passive sheath 12, may indicate the distal end of the passive sheath 12 is 1 cm proximal the distal tip of the distal shaft portion 13. Additional marks may be added for other relative positions between the passive sheath 12 and shaft 10, 50. The markings 35 may be printed on an outer diameter of the shaft 10, 50, may be visible through the shaft 10, 50, or other. Placement of the passive sheath 12 may be used to influence the curve shape of the distal segment 31 of the shaft 10, 50 by adding stiffness over the shaft 10, 50 at one or more points along the shaft 10, 50. Use of this relative placement of sheath 12 and shaft 10, 50 provides more curve shapes as may be needed in the variety of human anatomical variations.

One embodiment of a 6 French passive sheath 12 is shown. It is to be appreciated that the passive sheath 12 of FIG. 6 is described for illustrative purposes only and other embodiments of sheaths may be used with the catheter system 9. The 6 French passive sheath 12 may be a 0.100-0.105 in. outer diameter tube with a central lumen 44 constructed of a PTFE extrusion 43 with a wall thickness of 0.001 in., range of 0.0005-0.002 in. covered by a layer of Hytrel®, a braid of 0.001-0.003 in. stainless steel wire 45 and a second extrusion of Hytrel® over the braid 46. The composite wall thickness may be about 0.006-0.017 in. This provides a passive sheath inner diameter of approximately 0.082-0.087 in. Alternatively the passive sheath may be extruded of various combinations of polymers with no metal braid such that the sheath has adequate hoop strength and kink resistance and adequate pushability and flexibility to be easily passed over the shaft and the guidewire through the vasculature. The PTFE inner lumen 44 provides a low friction surface for passage over the shaft 10, 50 and also for passage of treatment catheters therethrough after the catheter 9 is removed. The passive sheath 12 may have a proximal hub 40 with a built-in hemostatic valve that may be bonded to the shaft 41 with epoxy 34. Optionally the hub 40 may have a female luer fitting adaptable for connection to a separate hemostasis valve. In the embodiment shown, the passive sheath 12 includes a braidless distal tip 42 that is tapered or rounded to ease entry through the subcutaneous tissue and arterial puncture when advanced over the shaft 10, 50. This distal tip 42 may be made from a polymer and bonded to the shaft 41 or may be made by removing braid from the tip of the shaft 41 and reflowing the Hytrel® in a dye with a tapered shape. Appropriate dimensional changes may be made for other French-sized passive sheaths.

FIGS. 8a and 8b illustrate an alternative arterial access system 100 embodiment. The arterial access system comprises a catheter having a shaft 102 and a handle 103. The shaft 102 may have segments of variable stiffness and a soft deflectable tip 106 at its distal end. In the embodiment of FIGS. 8a and 8b, the shaft 102 has a preset passive shape.

While pullwire deflection has been used in prior art systems, in those systems, the pullwire causes the catheter shaft to preferentially align in the anatomy such that the distal tip is deflected in the same direction as the catheter curvature. This alignment may force the distal tip of the catheter to deflect away form the desired direction for accessing vessels. The pullwire tension may also cause the catheter to resist torsional rotation, making deflecting the tip in the opposite direction difficult.

In contrast to such prior art systems, the shaft 102 of FIGS. 8a and 8b has a preset passive shape comprising curves 114a and 114b. As shown, the shape may be a broad curve or arch. The shape acts to preferentially align the shaft 102 in the aortic arch. The passive shape prevents catheter rotation during tip deflection because the shape mimics the arch, thereby directing the tip into the carotid arteries. In addition, the shape provides support when advancing guidewires or an access sheath into the carotid arteries. Generally, the shaft is more flexible towards the distal end 110 and stiffer towards the proximal end 116.

The shaft 102 is coupled to a handle 103 at its proximal end 116. The shaft 102 comprises a generally central lumen 108 for threading over a guidewire into the carotid arteries. It is to be appreciated that the lumen 108 may be centered or may be eccentric. The handle 103 may be as described with respect to the handle 16 previously described or may have other suitable configuration.

The tip 106 has a tapered shape and may act as a dilator to reduce vascular trauma as the catheter is advanced through vasculature. The distal end may have a hydrophilic coating to aid in shaft 102 delivery through the vasculature, as well as to aid in sheath advancement over the shaft 102.

Generally, the shaft 102 may have a preset shape or curvature. FIG. 8a illustrates a shaft 102 having first and second curves 114a and 114b. In various embodiments, the preset shapes or curves 114a, 114b may extend, for example, from the distal tip 106 approximately 25 centimeters up the shaft 102. Generally, the shaft may have a preset shape for any suitable length such as from approximately 1 centimeter to approximately 40 centimeters, or from approximately 20 centimeters to approximately 30 centimeters. The distal segment 110 of the shaft 102 is deflectable or steerable. Accordingly, the curvest 114a, 114b may have a pre-set shape to facilitate accessing specific anatomy. For example, the shaft 102 may have curves 114a, 114b having a preset shape similar to a neuroradiology angiography catheter. For example, the shaft 102 may have a preset shape comprising curves 114a and 114b as shown in FIG. 8a. As discussed with respect to the embodiment of FIGS. 2a-2c, the distal end 110 may be provided with a radiopaque marker for visualization. Thus, in one embodiment, the tip 106 may be manufactured of a radiopaque polymer to assist with fluoroscopic visualization.

A pullwire 112 is coupled to a pull collar at the distal tip 106. Pulling on the pullwire 112 curves the distal segment 110. The pullwire 112 may be provided along an outer surface of the shaft 102, may be provided within a lumen of the shaft 102, may be integrated into the wall of the shaft 102, or may be otherwise associated with the shaft 102. In the embodiment shown, the pullwire 112 is run through the wall of the shaft 102 on the side towards which the distal tip 106 deflects (see FIG. 8b). In one embodiment, the pullwire comprises a multi-stranded stainless steel wire. The pullwire 112 is pulled to deflect the distal tip 106. Pulling may be achieved in any suitable manner. In one embodiment, a pull collar is provided at or near the tip 106 and is attached to the pullwire 112. Pulling the pullwire 112 deflects the distal tip 106 in a direction opposite the curvature direction of pre-set curve 114a.

FIG. 8b shows a cross-section of the shaft 104. Description is made of the shaft 104 starting at its center and moving outwardly. In the embodiment shown, the central lumen 108 has a PTFE liner to reduce guidewire friction. In alternative embodiments, no liner may be provided or other suitable friction reducing material may be used. A braid 122 is provided for torque response and kink resistance. The braid 122 may be, for example, stainless steel or nitinol. A jacket 126 is provided over the braid 122 for variable stiffness. Thus, the thickness and/or make up of the jacket 126 may vary along the length of the shaft 104. In various embodiments, the jacket comprises a multi-durometer polymer jacket. In the embodiment of FIG. 9b, the pullwire 112 is provided in the wall of the shaft 104 between the PTFE inner lumen liner 120 and the braid 122. A PTFE liner 124 may be provided along an interior surface of the braid 122 to reduce friction with the pullwire 112.

Figure 9A:
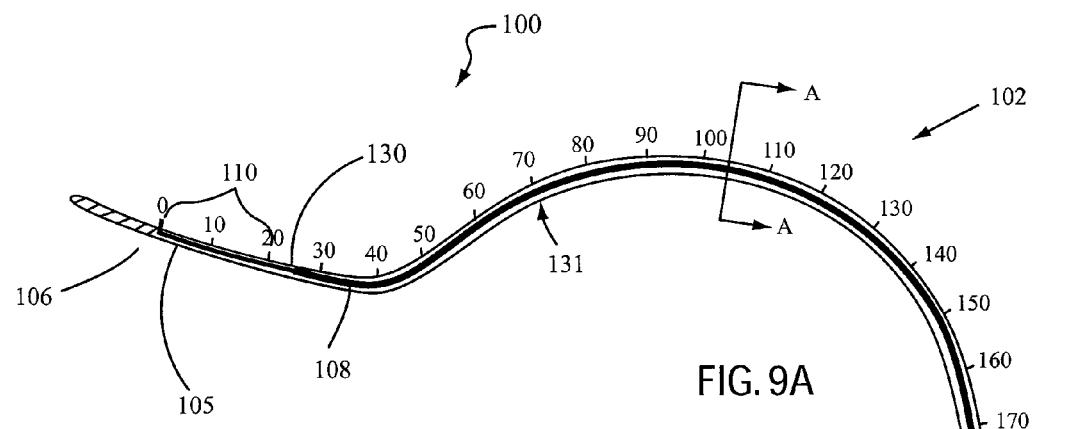
FIG. 9a is a perspective view of an arterial access system including a shaft and two pullwires to effect shaft deflection in accordance with one embodiment.
Figure 9B:
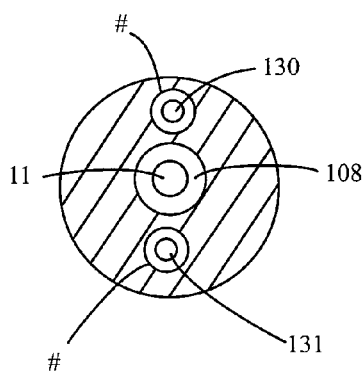
FIG. 9b is a cross-sectional view of the shaft of FIG. 9a in accordance with one embodiment.

FIGS. 9a and 9b illustrate an alternative embodiment of a vascular access system 100 comprising a shaft 102 and a handle 103. FIG. 9a illustrates a perspective view of the vascular access system 100. FIG. 9b illustrates a cross-section of the shaft 102 of the vascular access system.

In the embodiment shown in FIGS. 9a and 9b, the shaft 102 may be deflected in two separate curve shapes by utilizing first and second pullwires 130 and 131 in the shaft 102. Accordingly, in the embodiment of FIGS. 9a and 9b, the shaft 102 may not have a preset shape. It is noted, however, that the pullwires described in FIGS. 9a and 9b may be used with a shaft 102 having a present shape.

The first pullwire 130 is coupled to a distal pull collar 105 proximate the distal tip 106 of the shaft 102. The first pullwire 130 may be used to deflect the distal segment 110 of the shaft 102. The second pullwire 131 is coupled to a proximal pull collar 107 located proximal to the distal pull collar 130. The second pullwire 131 may be located on generally the opposite side of shaft 102. The second pullwire 131 may be used to deflect the shaft 102 in a direction opposite the deflection caused by the first pullwire 130 to form a broad curve that mimics the aortic arch geometry and provides stability to substantially prevent the shaft 102 from rotating during deflection of the distal segment 110. The second pullwire 131 may be fixed at the handle 103 to hold the shaft 102 in alignment within the arch geometry. The distal segment 110 may be deflected by pulling the first pullwire 130 to access the required vasculature.

Referring to FIGS. 8a, 8b, 9a, and 9b, in some embodiments, an access sheath may be preloaded over the shaft 102. In other embodiments, an access sheath may be advanced over the shaft 102 after the shaft 102 is placed in the artery.

Figure 10:
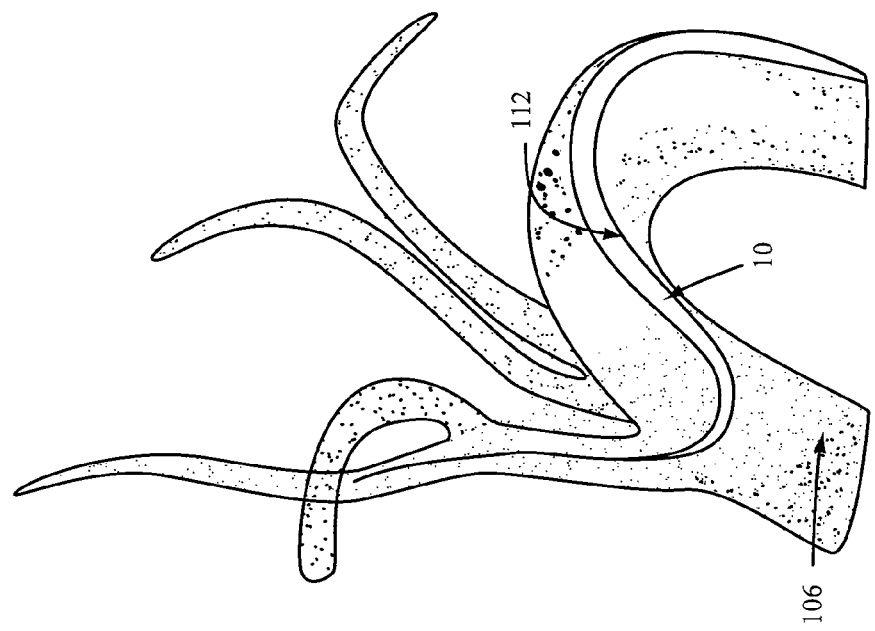
FIG. 10 is a view of the shaft of FIG. 8a or 9a deployed in a Type III Aortic Arch in accordance with one embodiment.

FIG. 10 illustrates an arterial access system 100 such as described with reference to FIGS. 8a and 8b or 9a and 9b placed within a Type III Aortic Arch. Using the embodiment of FIGS. 8a and 8b, the shaft 102 assumes the initial passive shape when in the aortic arch. Using the embodiment of FIGS. 9a and 9b, the shaft 102 is deflected within the aortic arch using pullwires 130 and 131.

Once femoral artery access is obtained with a guidewire in place in the artery and puncture track, for example by a Seldinger Technique using a 0.035 or 0.038 in. guidewire, the following method of use of the carotid access systems herein described may be employed. It is to be appreciated that the described method is illustrative only and other methods of using the carotid access systems may be obvious to those skilled in the art.

a) Advance the guidewire through the femoral and iliac arteries, descending aorta and into the aortic arch;

b) With the passive sheath preloaded on the shaft, back load the guidewire into the distal end of the shaft, and advance the shaft over the guidewire through the subcutaneous tissue and into the femoral artery;

c) Advance the passive sheath over the shaft and into the femoral artery;

d) Advance the passive sheath/shaft combination over the guidewire with the distal tip of the shaft extending beyond the sheath, to the aortic arch area of carotid or braciocephalic artery take off;

e) With the guidewire tip just beyond the distal tip of the shaft, manipulate the handle to cause a desired deflection of the tip of the shaft and rotate the handle to orient the deflected tip toward the desired ostium;

f) Advance the guidewire through the ostium along the desired path toward the treatment area of interest;

g) Advance the passive sheath over the shaft and guidewire along the desired path toward the area of treatment;

h) If the passive sheath can be advanced to just proximal the area of treatment, manipulate the handle to relax the deflected tip and remove the shaft and guidewire while holding the sheath in place; (skip to step j)

i) If the passive sheath can not be advanced to the area of treatment, manipulate the handle to relax the deflected tip and advance the shaft over the guidewire to the next branch point and repeat steps e through h;

j) Introduce the treatment catheters/devices and treat the lesion (PTCA, stents, embolic protection, guidewire, etc.);

k) Remove the treatment catheters/devices;

l) Remove the passive sheath;

m) Seal the arterial puncture as well known in the art.

In some instances step "a" may be eliminated if step "d" includes advancing the guidewire along with the shaft/sheath, for example, as long as the guidewire is advanced beyond the distal tip of the shaft by a few centimeters to protect the artery from being damaged by the shaft tip.

While several illustrative embodiments of the invention have been shown and described, numerous variations and alternate embodiments will occur to those skilled in the art. Further, it is to be appreciated that while the systems have been specifically described with reference to accessing the carotid arteries, the systems may be applied to any vasculature. Such variations and alternate embodiments are contemplated, and can be made without departing from the spirit and scope of the invention as defined in the appended claims.

What is claimed is:

1. A system for arterial access for delivery of one or more treatment devices, the system comprising:
a guidewire,
a handle;
a shaft, the shaft having a proximal end and a distal end, the proximal end being coupled to the handle and a distal segment of the shaft proximate the distal end being deflectable, wherein the shaft has a pre-set curvature comprising at least one curve along the length of the shaft, the pre-set curvature being proximal of the distal segment, and has a lumen for receiving the guidewire at least partially there through;
a pullwire coupled to the shaft such that actuation of the pullwire deflects the distal segment of the shaft in a direction opposite the pre-set curvature; and
a sheath adapted to be delivered over the shaft.

2. The system of claim 1, wherein a length of the guidewire is longer than a length of the shaft, and the length of the shaft is longer than a length of the sheath.

3. The system of claim 1, wherein the shaft comprises a proximal shaft portion and a distal shaft portion, the distal shaft portion comprising a restoring force member.

4. The system of claim 3, further comprising a transition member between the proximal shaft portion and the distal shaft portion.

5. The system of claim 1, the shaft having a distal end diameter and the sheath having a distal end diameter, the system further comprising a dilator distal tip tapered between the distal end diameter of the shaft to the distal end diameter of the sheath.

6. The system of claim 1, wherein the sheath may be manipulated to effect the curvature of the shaft such that positioning a distal end of the sheath nearer the distal end of the shaft results in a tighter curvature of the distal tip.

7. A system for arterial access for delivery of one or more treatment devices, the system comprising:
a guidewire,
a handle;
a shaft, the shaft having a proximal end and a distal end, the proximal end being coupled to the handle and a distal segment of the shaft proximate the distal end being deflectable, wherein the shaft has a pre-set curvature comprising at least one curve along the length of the shaft, the pre-set curvature being proximal of the distal segment, and wherein the shaft has a lumen for receiving the guidewire at least partially there through;
first and second pullwires being associated with the shaft, wherein the first pullwire is coupled to the shaft at a first coupling point that is proximate the distal end of the shaft and the second pullwire is coupled to the shaft at a second coupling point positioned proximally of the first coupling point, the first pullwire effecting a curvature of the shaft in a first direction and the second pullwire effecting a curvature of the shaft in a second direction opposite the first direction; and
a sheath adapted to be delivered over the shaft.

8. The system of claim 7, wherein a length of the guidewire is longer than a length of the shaft, and the length of the shaft is longer than a length of the sheath.

9. The system of claim 7, wherein the shaft comprises a proximal shaft portion and a distal shaft portion, the distal shaft portion comprising a restoring force member.

10. The system of claim 7, the shaft having a distal end diameter and the sheath having a distal end diameter, the system further comprising a dilator distal tip tapered between the distal end diameter of the shaft to the distal end diameter of the sheath.

11. The system of claim 6, wherein the sheath may be manipulated to effect the curvature of the shaft such that positioning a distal end of the sheath nearer the distal end of the shaft results in a tighter curvature of the distal tip.

12. A method of treating carotid artery lesions comprising:
providing a system comprising a guidewire, a shaft having a pre-set curvature, a deflectable tip, the tip being deflected in a direction opposite the pre-set curvature upon manipulation of a pullwire, and a lumen for passage over the guidewire, and a sheath sized for placement over the shaft;

accessing a femoral artery with a needle;

placing the guidewire through the needle and into the femoral artery;

removing the needle;

advancing the shaft, having the sheath overlying the shaft, over the guidewire and into and through the femoral artery to an aortic arch;

manipulating the shaft to direct the deflectable tip toward the ostium leading to a right or a left carotid artery;

advancing the guidewire through the ostium into the carotid artery;

advancing the shaft over the guidewire into the carotid artery;

advancing the sheath over the shaft and into the carotid artery;

removing the guidewire and shaft;

introducing one or more treatment devices through the sheath;

treating one or more carotid lesions;

removing the treatment devices from the sheath;

removing the sheath from the body; and sealing the puncture site at the femoral artery.

13. A method of establishing femoral access to the carotid artery, suitable for passage of carotid artery lesion treatment devices, comprising:

providing a system comprising a guidewire, a shaft having a lumen for passage over the guidewire, wherein the shaft may be manipulated to pre-set curvature, and a sheath sized for placement over the shaft;

accessing a femoral artery with a needle;

placing a guidewire through the needle and into the femoral artery; removing the needle;

advancing the shaft, having the sheath overlying the shaft, over the guidewire and into and through the femoral artery to an aortic arch;

manipulating the shaft to direct a deflectable tip toward the ostium leading to a right or a left carotid artery, the tip being deflected in a direction opposite the pre-set curvature upon manipulation of a pullwire;

advancing the guidewire through an ostium into a carotid artery;

advancing the sheath over the shaft and into the carotid artery; and removing the guidewire and shaft.

14. An arterial access system comprising:

a handle;

and a shaft, the shaft comprising:

a distal end and a proximal end wherein the shaft has varying stiffness along a length thereof, being most stiff at the proximal end and least stiff at the distal end, a pre-set curvature along the length of the shaft;

a distal tip at the distal end of the catheter, wherein the distal tip may be deflected by actuation of the handle, wherein the pre-set curvature is proximal of the distal tip; and a pullwire, the pullwire being provided along the length of the shaft extending from the distal tip to the handle such that actuation of the handle pulls the pullwire and deflects the distal tip in a direction opposite the pre-set curvature.

15. The arterial access system of claim 14, wherein the shaft has a pre-set curvature.

16. The arterial access system of claim 14, further comprising first and second pullwires associated with the shaft, the first pullwire being coupled to the shaft proximate the distal end of the shaft and the second pullwire being coupled to the shaft proximally of the distal end of the shaft, the first and second pullwires effecting a curvature of the shaft.

17. The access system of claim 14, wherein the distal tip acts as a dilator.

\* \* \* \* \*